United States Patent
Kump et al.

(10) Patent No.: US 6,931,098 B2
(45) Date of Patent: Aug. 16, 2005

(54) METHOD AND SYSTEM FOR DUAL OR MULTIPLE ENERGY IMAGING

(75) Inventors: Kenneth Scott Kump, Waukesha, WI (US); Jibril Odogba, Waukesha, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 528 days.

(21) Appl. No.: 09/683,992

(22) Filed: Mar. 8, 2002

(65) Prior Publication Data

US 2003/0169850 A1 Sep. 11, 2003

(51) Int. Cl.⁷ ............................................. H05G 1/64
(52) U.S. Cl. ..................... 378/98.9; 378/98.8; 378/19
(58) Field of Search ............................ 378/98.9, 98.11, 378/98.12, 5, 19, 98.8, 207

(56) References Cited

U.S. PATENT DOCUMENTS

| | | | |
|---|---|---|---|
| 6,018,562 A | * | 1/2000 | Willson .......................... 378/9 |
| 6,115,451 A | | 9/2000 | Boudry et al. ............. 378/98.8 |
| 6,343,112 B1 | | 1/2002 | Petrick et al. ............. 378/98.9 |
| 6,418,189 B1 | * | 7/2002 | Schafer ....................... 378/57 |

* cited by examiner

*Primary Examiner*—David V. Bruce
*Assistant Examiner*—Irakli Kiknadze
(74) *Attorney, Agent, or Firm*—Cantor Colburn LLP

(57) ABSTRACT

A method minimizing artifacts in dual or multiple energy images includes: obtaining first and second offset images from a detector after obtaining first and second exposure image data sets from the detector. Other embodiments include: changing the dosage of the exposures, changing the gain of the detector, changing the pixel acquisition resolution of the detector, and leaving the detector unscrubbed between the first and second read times.

30 Claims, 4 Drawing Sheets

METHOD AND SYSTEM FOR DUAL OR MULTIPLE ENERGY IMAGING

BACKGROUND OF INVENTION

The present disclosure relates generally to dual or multiple energy imaging and in particular, to a detector acquisition sequence and system for dual or multiple energy imaging to minimize artifacts and total exam time between acquisitions.

The classic radiograph or "X-ray" image is obtained by situating the object to be imaged between an X-ray emitter and an X-ray detector made of photographic film. Emitted X-rays pass through the object to expose the film, and the degree of exposure at the various points on the film are determined by the density and thickness of the object along the path of the X-rays.

X-ray images may be used for many purposes. For instance, internal defects in a target object may be detected. Additionally, changes in internal structure or alignment may be determined. Furthermore, the image may show the presence or absence of objects in the target. The information gained from x-ray imaging has applications in many fields, including medicine and manufacturing.

It is now common to utilize solid-state digital X-ray detectors (e.g., an array of switching elements and photosensitive elements such as photodiodes) in place of film detectors. The charges generated by the X-rays on the various points of the detector are read and processed to generate a digital image of the object in electronic form, rather than an analog image on photographic film. Digital imaging is advantageous because the image can later be electronically transmitted to other locations, subjected to diagnostic algorithms to determine properties of the imaged object, and so on.

One embodiment of a solid state digital x-ray detector may be comprised of a panel of semiconductor Field Effect Transistors (FETs) and photodiodes. The FETs and photodiodes in the panel are typically arranged in rows (scan lines) and columns (data lines). A FET controller controls the order in which the FETs are turned on and off. The FETs are typically turned on, or activated, in rows. When the FETs are turned on, charge to establish the FET channel is drawn into the FET from both the source and the drain of the transistor. Due to the imperfect nature of the amorphous silicon FETs, the charge is retained temporarily when the FET is turned off and bleeds out, decaying, over time, which corrupts the desired signal in the form of an offset. The source of each FET is connected to a photodiode. The drain of each FET is connected to read-out electronics via data lines. Each photodiode integrates the light signal and discharges energy in proportion to the x-rays absorbed by the detector. The gates of the FETs are connected to the FET controller. The FET controller allows signals discharged from the panel of photodiodes to be read in an orderly fashion. The read-out electronics convert the signals discharged from photodiodes. The energy discharged by the photodiodes in the detector and converted by the read-out electronics is used by an acquisition system to activate pixels in the displayed digital diagnostic image. The panel of FETs and photodiodes is typically scanned by row. The corresponding pixels in the digital diagnostic image are typically activated in rows.

The FETs in the x-ray detector act as switches to control the charging and discharging of the photodiodes. When a FET is open, an associated photodiode is isolated from the read-out electronics and is discharged during an x-ray exposure. When the FET is closed, the photodiode is recharged to an initial charge by the read-out electronics. Light is emitted by a scintillator in response to x-rays absorbed from the source. The photodiodes sense the emitted light and are partially discharged. Thus, while the FETs are open, the photodiodes retain a charge representative of the x-ray dose. When a FET is closed, a desired voltage across the photodiode is restored. The measured charge amount to re-establish the desired voltage becomes a measure of the x-ray dose integrated by the photodiode during the length of the x-ray exposure.

One source of difficulty faced by digital x-ray systems is the photoconductive characteristics of semiconductor devices used in the digital x-ray systems. Photoconductivity is an increase in electron conductivity of a material through optical (light) excitation of electrons in the material. Photoconductive characteristics are exhibited by the FETs used as switches in solid state x-ray detectors. Ideally, FET switches isolate the photodiode from the electronics, which measure the charge restored to the photodiode. FETs exhibiting photoconductive characteristics do not completely isolate the photodiode from the system, when the FETs are open. Consequently, the FETs transfer excess charge to the read-out electronics. If the FETs transfer excess charge to the read-out electronics, the energy subsequently discharged from the photodiodes to activate the pixels in the digital image may be affected. The unintended charge leakage through the FETs may produce artifacts or may add a non-uniform offset value to each of the pixels in the digital x-ray image, thus producing a line artifact in the image.

FETs and other materials made of amorphous silicon also exhibit a characteristic referred to as charge retention. Charge retention is a structured phenomenon and be controlled to a certain extent. Charge retention corresponds to the phenomenon whereby not all of the charge drawn into the FET to establish a conducting channel is forced out when the FET is turned off. The retained charge leaks out of the FET over time, even after the FET is turned off, and the leaked charge from the FET adds an offset to the signal read out of the photodiodes by the x-ray control system.

The FETs in the x-ray detector exhibit charge retention characteristics when voltage is applied to the gates of the FETs to read the rows of the x-ray detector. The detector rows are generally read in a predetermined manner, sequence, and time interval. The time interval may vary between read operations for complete frames of the x-ray image. When a FET is opened after the charge on an associated photodiode is read by a charge measurement unit, the FET retains a portion of the charge. Between read operations, the charge retained by the FETs leaks from the FETs to a charge measurement unit. The amount of charge that leaks from the FETs exponentially decays over time. The next read operation occurs before the entire retention charge leaks from the FETs. Consequently, the charge measurement unit measures during each read operation an amount of charge that is retained by the FETs during the read operation for the present scan line. The charge measurement unit also reads an amount of charge that was stored by FETs that were activated in scan lines preceding (in time) the current scan line in both the current (detector) read operation and the preceding (detector) read operation.

The charge leaking from the FETs when a new read operation is initiated is referred to as the initial charge retention. The initial charge retention stored on multiple FETs, such as the FETs of a single data line, combines to form a charge retention offset for that column. The charge retention offset varies based on the rate at which rows of the x-ray detector panel are read. As the interval increases between read operations, the charge decay increases. As the panel rows are read, the charge retention offset builds to a steady state value. The steady state value for the charge retention rate represents the point at which the panel rows are read at a rate equaling the exponential decay rate of the charge on the FETs.

During an x-ray exposure, a similar phenomenon occurs whereby charge is generated in the FET as a result of the FET photoconductive characteristics. When the FETs are turned off at the end of the exposure, the additional charge also leaks out and adds to the read signal in a manner analogous to charge retention. However, the additional charge cannot be removed because the additional charge, resulting from the FET photoconductive characteristics, relates to the x-rays bombarding the x-ray detector. The number of FETs that photoconduct and the amount of charge conducted by the FETs are dependent upon the amount of x-ray exposure and the object imaged, as well as upon the individual properties of each FET. Since a solid state x-ray detector is structured along rows (scan lines) and columns (data lines), the excess charge in the FETs may result in structured image artifacts (e.g., pixels, lines, shapes) or offsets.

During the digital imaging process, the image is generally not produced directly from the detector reading. Instead, the detector reading is processed to produce a cleaner image. In particular, the image is usually processed to eliminate the "offset", which arises owing to the photoconductive characteristics of the detector prior to the time the exposure is made. The qualities of the offset are determined by the detector's current leakage, temperature, background radiation, and a variety of other factors. The offset is desirably eliminated from the detector reading to provide better image quality.

In dual-energy imaging, two sequential X-ray acquisitions are made using different X-ray spectra to produce a bone only and a soft tissue only image, which enhances the visualization of nodules and calcification. The X-ray spectrum is modified by the X-ray generator energy and/or spectral filters being utilized. To minimize patient motion between the two acquisitions, they are acquired as close together as possible in time. Patient motions between the two acquisitions will cause artifacts in the dual-energy images.

For a digital radiographic (DR) system operated in a dual energy mode, the detector must be read between the two exposures. The "normal" radiographic acquisition sequence includes: a first X-ray dosage ($Xray_1$), a first delay following the first X-ray dosage ($Delay_1$) a first read following the first delay ($Read_1$), a first X-ray dosage following the first read ($Xray_2$), a second delay following the second X-ray dosage ($Delay_2$), and a second read following the second delay ($Read_2$). Typically, a number of detector "scrubs" are made between exposures $Xray_1$ and X-$ray_2$. These scrubs are a detector reading without x-ray exposure, and serve to maintain the electrical stability of the amorphous silicon FETs and reduce the image lag.

To ensure that the detector is read as fast as possible without artifacts due to patient motion, the e-ray acquisitions should be as close as possible. To ensure that the X-ray acquisitions are as close together as possible, the critical time to minimize is equal to the sum of the duration of $Xray_1$, the duration of $Delay_1$, the duration of $Read_1$, and the duration of $Xray_2$. Typical values for these parameters are: $Xray_1$ 50 milliseconds, $Delay_1$ 50 milliseconds, $Read_1$ 80 milliseconds, and $Xray_2$ 50 milliseconds. Thus, the estimate of this critical time is 50+50+180+50=320 milliseconds. Clinical and research studies have suggested that a critical time of 50 milliseconds is needed to freeze the motion of the heart and the pressure wave that conducts through the lungs during a dual-energy chest exam in order to completely eliminate artifacts due to patient motion.

Other medical imaging applications where this critical time is of importance includes bone mineral densitometry (BMD) and tomosynthesis. Although BMD uses the dual energy application, spatial resolution is not critical because the current state of the art systems use a 1 $mm^2$ pixel pitch. Tomosynthesis is performed by acquiring multiple images with a digital detector, i.e. series of low dose images used to reconstruct tomography images at any level. Tomosynthesis may be performed using many different tube motions including linear, circular, elliptical, hypocycloidal, and others. In tomosynthesis, image sequences are acquired, with typical number of images ranging from 5 to 50.

Fast acquisition techniques in general have the propensity to cause artifacts in solid-state detectors. With any image acquisition, artifacts must be minimized and/or eliminated to prevent an impairment of the diagnostic value of the images. These artifacts include, but are not limited to pixels, lines, and shapes artifacts. Examples of the causes of these artifacts include lag, gain hysteresis, and timing mode changes. These artifacts may appear in any of the x-ray images or offset images. As such, the fast imaging read scenario must optimize the critical time without introducing any image artifacts.

SUMMARY OF INVENTION

The above discussed and other drawbacks and deficiencies are overcome or alleviated by a method minimizing artifacts in dual or multiple energy images. The method includes: exposing a detector to a first exposure from an energy source during a first exposure interval; after said first exposure interval, obtaining a first image data set during a first read time; after the first read time, exposing the detector to a second exposure from the energy source during a second exposure interval; after the second exposure interval, obtaining a second image data set during a second read time; after the second read time, scrubbing the detector; after the scrubbing, obtaining a first offset image from the detector; after the obtaining the first offset image, obtaining a second offset image from the detector; applying the first offset image to compensate for charge retention effects in the first image data set; and applying the second offset image to compensate for charge retention effects in the second image data set.

In one embodiment of the invention, the method includes repeating these steps for a plurality of frames. Other embodiments include: changing the dosage of the exposures, changing the gain of the detector, changing the pixel acquisition resolution of the detector, and leaving the detector unscrubbed between the first and second read times.

The above discussed and other features and advantages of the present invention will be appreciated and understood by those skilled in the art from the following detailed description and drawings.

BRIEF DESCRIPTION OF DRAWINGS

Referring to the exemplary drawings wherein like elements are numbered alike in the several Figures.

DETAILED DESCRIPTION

Figure 1:
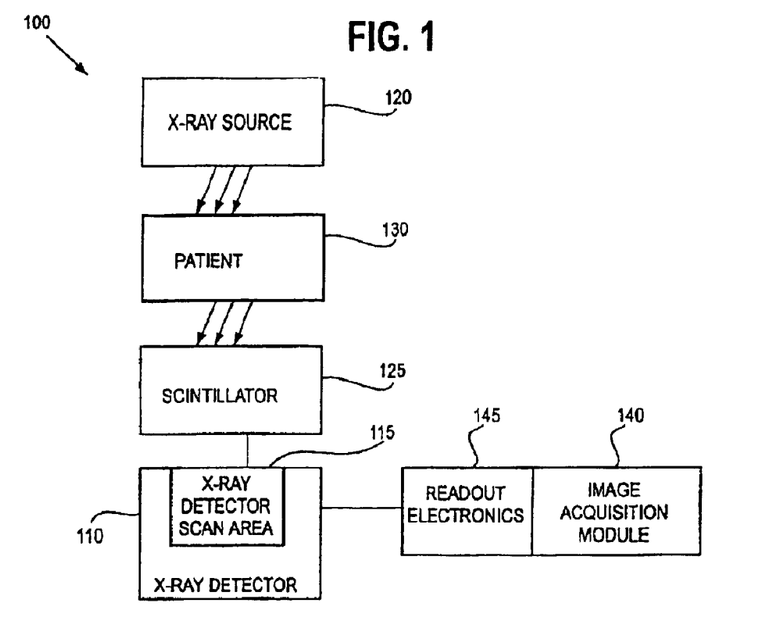
FIG. 1 is a schematic diagram of an imaging system.

FIG. 1 illustrates an imaging system 100 used in accordance with a preferred embodiment of the present invention. The imaging system 100 includes a plurality of subsystems. For the purposes of illustration only, the imaging system 100 is described as dual mode x-ray system. It will be recognized that the present invention may be applied to other modalities as well, such as, for example, gamma rays. In addition, it will be recognized that the present invention may be applied to multiple image systems such as, for example, tomosynthesis systems. Tomosynthesis is performed by acquiring multiple images (typically 5 to 50 images) with a digital detector to reconstruct tomography images. Tomosynthesis may be performed using many different tube motions including linear, circular, elliptical, hypocycloidal, and others.

The imaging system 100 includes subsystems, such as an x-ray detector 110, an x-ray detector scan area 115, an x-ray source 120, a scintillator 125. The imaging system 100 also includes an image acquisition unit 140 with read-out electronics 145.

A patient 130 or target object is positioned in the imaging system 100. An x-ray source 120 is positioned above the patient 130. The x-ray detector 110 is positioned below the patient 130. The scintillator 125 is positioned between the patient 130 and the x-ray detector 110. X-rays are transmitted from the x-ray source 120 through the patient 130 to the scintillator 125. The scintillator 125 emits light in response to the x-rays transmitted from the x-ray source 120 through the patient 130. The emitted light is transmitted to the x-ray detector 110 and the x-ray detector scan area 115.

Figure 2:
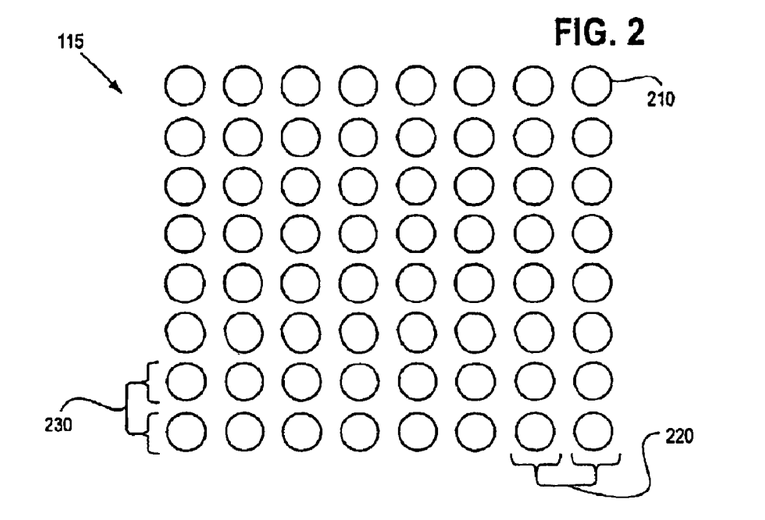
FIG. 2 is a plan view of a solid state x-ray detector.

FIG. 2 illustrates an example of a solid state x-ray detector scan area 115 within the x-ray detector 110. The x-ray detector scan area 115 is comprised of cells 210 corresponding to pixels in an x-ray image. The cells 210 may be arranged in columns 220 and rows 230. The cells 210 are controlled by scan lines along row 230 and read out by data lines along column 220. One or more cells 210 are uniquely mapped to one or more pixels in an x-ray image. The pixels are activated to produce the desired digital x-ray image of the patient 130.

Figure 3:
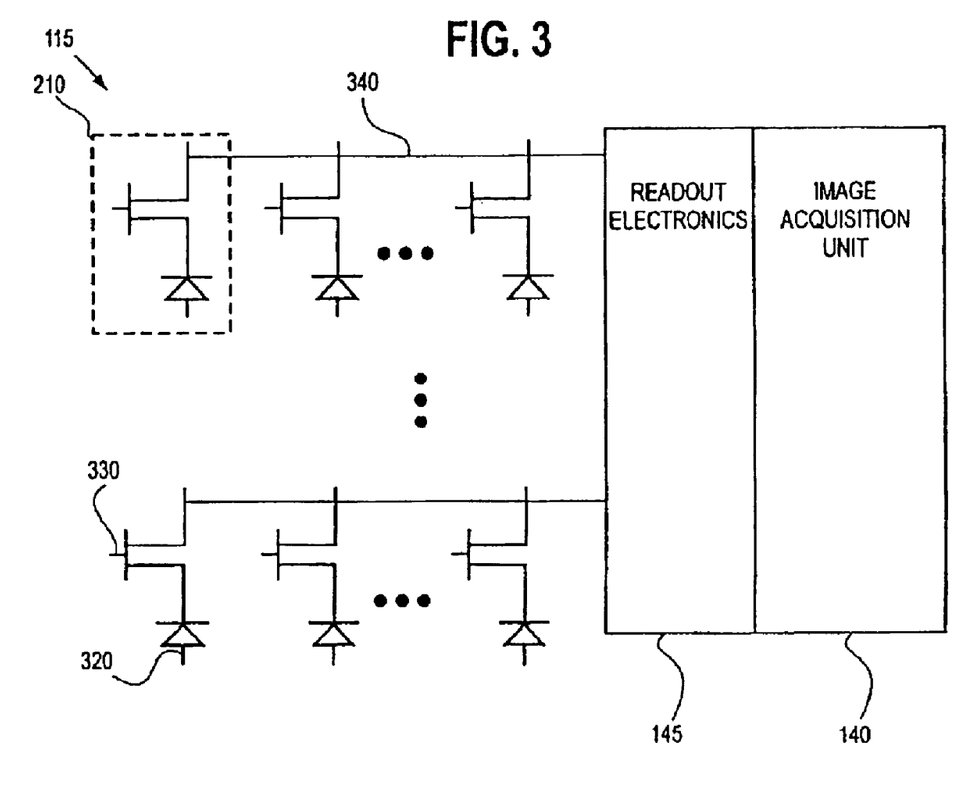
FIG. 3 is a schematic diagram of the solid state x-ray detector.

FIG. 3 is an example of a lower-level view of the solid state x-ray detector scan area 115 within the x-ray detector 110. Each cell 210 comprises a photodiode 320 and a Field Effect Transistor (FET) 330. Data lines 340 connect the cells 210 to the read-out electronics 145 of the image acquisition module 140. Through the read-out electronics 145, the image acquisition unit 140 acquires an x-ray image from the x-ray detector scan area 115.

The image acquisition module 140 may acquire an x-ray image from the x-ray detector scan area 115 by receiving a signal from the data lines 340 from the cells 210 in the x-ray detector scan area 115. The signal from the data lines 340 may be generated by charge stored in the photodiodes 320. The charge stored in the photodiodes 320 may result from absorption of light by the photodiodes 320. The light is emitted by the scintillator 125 directly above the photodiodes 320 in response to absorption of x-ray energy by the scintillator 125. The FETs 330 allow the charge stored in the photodiodes 320 to travel as a signal through the data lines 340. The FETs 330 may be actuated by the FET controller (not shown) in the image acquisition module 140. The signal received by the image acquisition module 140 may include an offset produced by the charge retention characteristics and photoconductive effects of the FETs 330.

Figure 4:
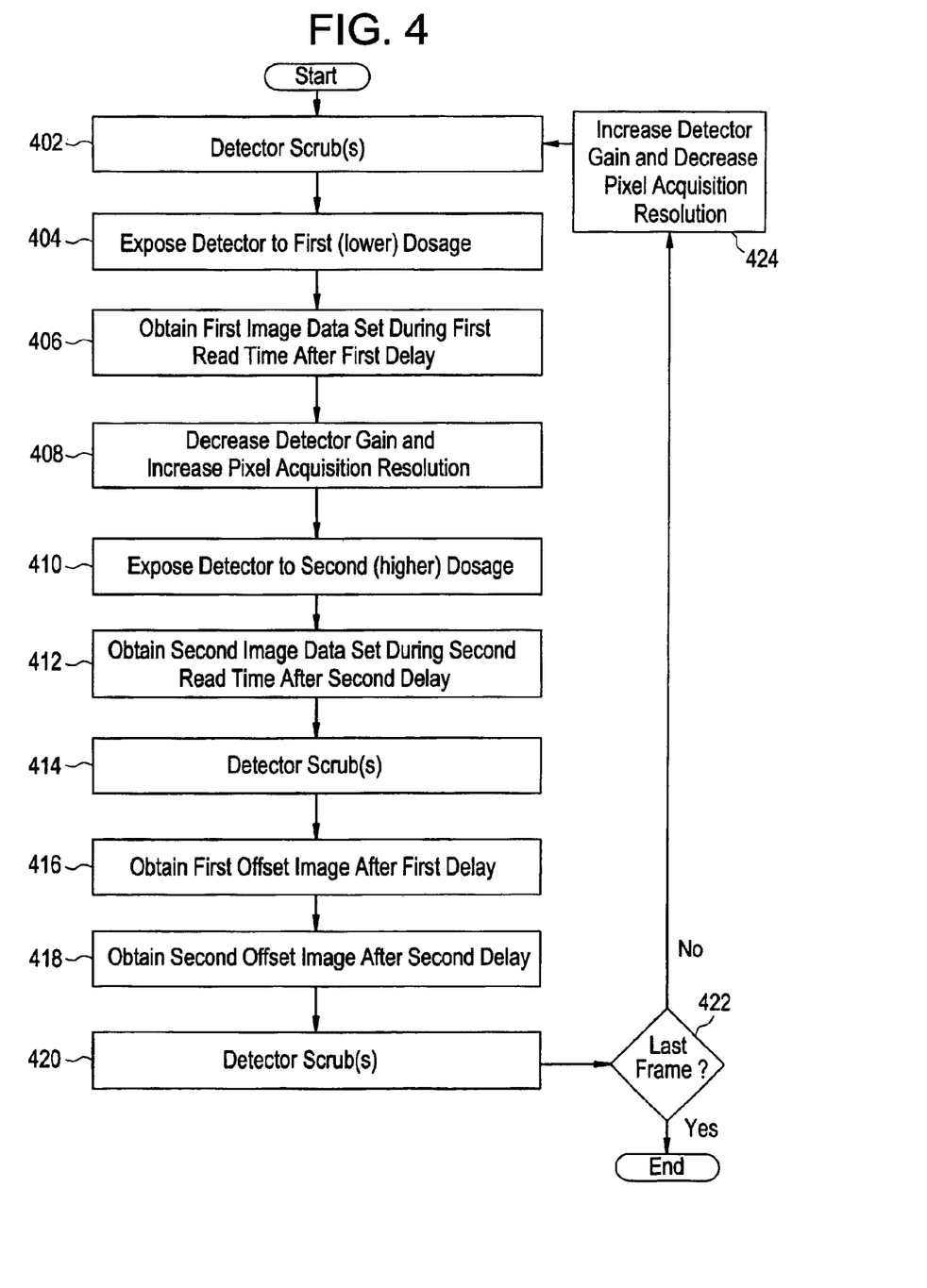
FIG. 4 is a flow chart depicting the general operation of the diagnostic imaging system of FIG. 1.
Figure 5:
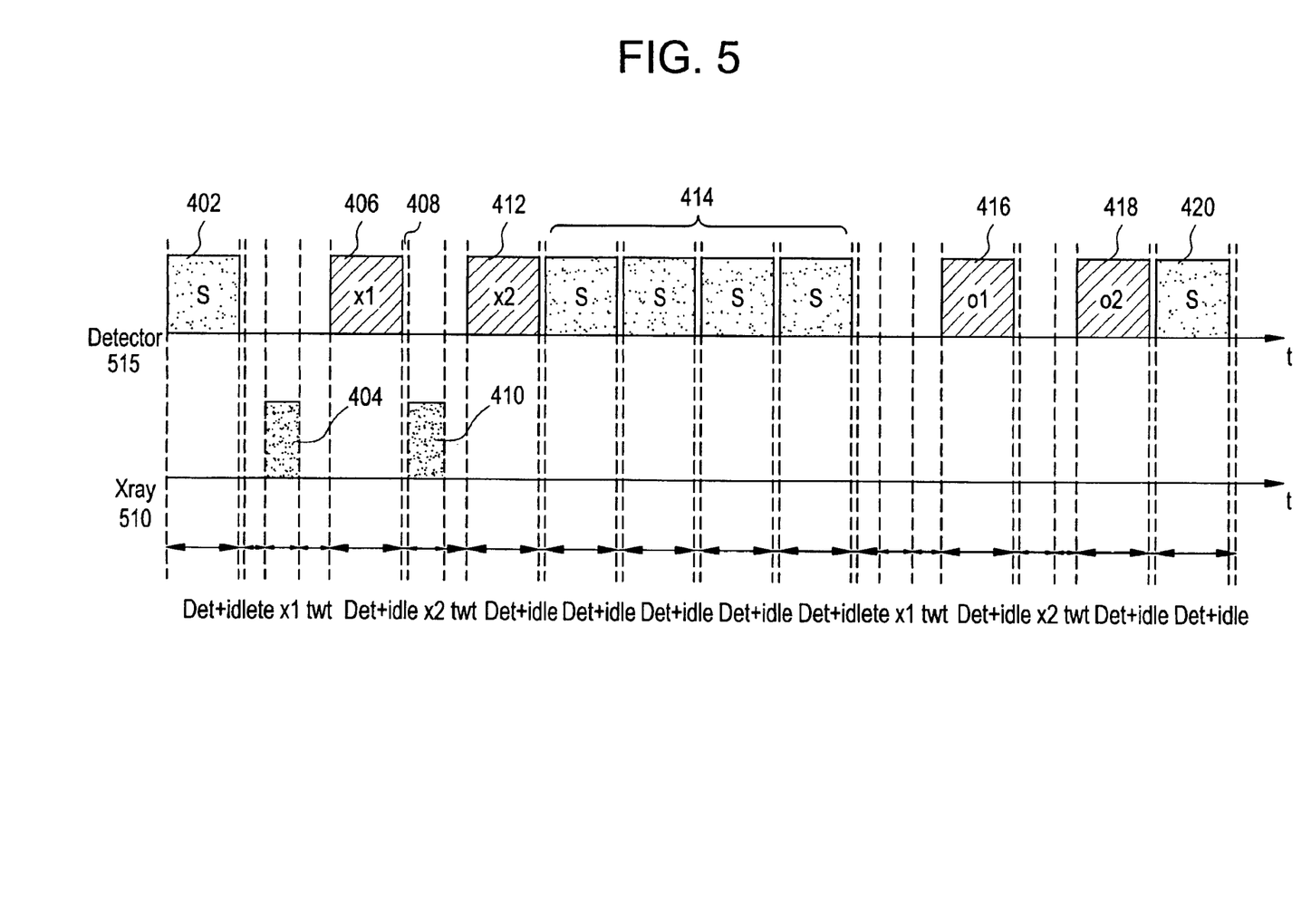
FIG. 5 is a plot illustrating an exemplary imaging sequence for the diagnostic imaging system of FIG. 1.

Operation of system 100 can be described generally with reference to the flow chart of FIG. 4 and the acquisition sequence time line of FIG. 5. Referring first to FIG. 5, line 510 denotes the exposure control signal that controls exposure sequence and timing wherein the x-ray source 120 is turned on when exposure signal 510 is high and off when the signal 510 is low. Line 515 denotes an acquisition control signal that controls the sequence and timing with which data is read from the detector 110. The various steps of FIG. 4, described below, are indicated in their respective time steps of FIG. 5.

In step 402 of FIG. 4, the detector 110 is "scrubbed" one or more times. That is, a detector read is performed without exposure and without sending image data. In step 404 of FIG. 4, the detector 110 is exposed to a first exposure from an energy source 120. In a preferred embodiment, the first exposure is a lower dose exposure, which will produce a darker image. A darker image may have less photoconductive effect than a brighter image. In step 406, a first set of image data is obtained from the first exposure. The first set of image data is obtained following a first delay. Preferably, the first delay is the minimum delay to reduce the photoconductive effects of the darker image. Typically, photoconductive effects are less in a darker image than a brighter image. Thus, the delay time for a darker image is less than the delay time for a brighter image. The first set of image data may be obtained from the detector 110 during a first read time. Preferably, the first read time is less than the second read time because the first image data set comprises a darker image data set with a smaller dynamic range than the image resulting from the second, higher dose exposure. The darker image with a smaller dynamic range may use fewer conversion levels to convert the data for each line 340 of the detector 110.

In step 408 the detector 110 gain is decreased. For example, the gain of the individual FETs 330 may be increased. By decreasing the gain of detector 110, the pixels generated in response to the second (higher) exposure and the first (lower) exposure are normalized.

Also in step 408, the pixel acquisition resolution is increased from that used in step 406 for acquiring the first set of image data. The reduced pixel acquisition resolution used for acquiring the first set of image data may be accomplished, for example, by pixel binning. That is, by acquiring data from fewer than all of the cells 210 in detector 110. For example if detector 110 is a 2048×2048 pixel element detector (2048×2048 cells), then the reduced pixel acquisition image may be read using only the output from 1024×1024 of the cells. This can be accomplished by "binning" the pixels during the read process. For example, 2×2 binning involves combining each group of 4 pixels (2 in column direction, 2 in row direction) into a single pixel. This reduces the image size to 1024×1024 cells. The advantage is that 1024×1024 pixels can be read out and transferred faster (50% for 2×2) which reduces the amount of time between any two xray pulses. The cost is image resolution. The time interval is weighed against the resolution to optimize the overall process. In step 408, the resolution is increased so that the higher resolution image (e.g., the 2048×2048 cell image) is used in the second (higher) exposure of step 410.

In step 410, the detector 110 is exposed to a second exposure from the energy source 120. Preferably, the second exposure is a higher dose exposure. Typically, a higher dose exposure will produce a brighter image. In step 412, a second set of image data is obtained from the second exposure. The second set of image data is obtained following a second delay. The second set of image data is obtained from the detector 110 during a second read time. The second read time may be longer than the first read time. The brighter image caused by the higher (second) exposure has a larger dynamic range than the darker image caused by the lower (first) exposure. The larger dynamic range may use more conversion levels than the darker image.

In step 414, the detector 110 is again scrubbed one or more times. Notable is the lack of scrubs between the exposures in steps 404 and 410. In a typical radiographic sequence, many scrubs (typically four or more) are issued between x-ray exposures. This serves to maintain the electrical stability of the amorphous silicon substrate and to reduce the image lag. In the present invention, the management of offset and lag allows the scrubs to be performed after the second image data set is obtained, thereby reducing the critical time between exposures.

In step 416, the detector 110 obtains a first offset image. An offset image is a "dark" scan in which the FETs on detector 110 are activated and data are recorded. The time between frames for both the first offset image of step 416 and the first image data set of step 406 are consistent, allowing the effect of charge retention in the FETs to be determined. That is, the time from the end of 402 to the beginning of 406 is the same as the time from the end of 414 to the beginning of 416. By subtracting the "dark" scan from the actual "exposed" scan of the desired object, the charge retention effects on the first image data set of step 406 may be eliminated.

In step 418, the detector 110 obtains a second offset image. As with the first offset image, the time between frames for both the second offset image of step 418 and the second image data set of step 410 are consistent, allowing the effect of charge retention in the FETs to be determined. By subtracting the "dark" scan from the actual "exposed" scan of the desired object, the charge retention effects on the second image data set of step 406 may be eliminated.

The embodiment shown in FIG. 4 is preferably used in a system 100 employing automatic exposure control (AEC). A system with AEC utilizes an x-ray sensitive ion chamber coupled with integrating electronics and a feedback control signal to control the xray source 120. The setup of the AEC includes setting the desired xray level (typically by the operator), which is translated into an integrated voltage threshold through a calibrated transfer function. During operation, the integrator circuit is reset, xrays are enabled, and the xray level integrated until its threshold is reached, at which time, the controlling signal terminates the xray. During this operation the actual exposure time is not known apriori. The digital detector and its offset are sensitive to the time between frames. Thus, in the embodiment of FIG. 4, the consistency of the timing between the xray acquisition and the offset acquisition is maintained.

Where the system is under manual control, rather than under the control of the AEC, the detector timing is known and is set to be the same for all xray images in an image sequence. Since the timing is the same for all xray frames, only a single offset is needed and is acquired at the same timing as the xray. Accordingly, in an embodiment where system 100 employs manual control, only one offset acquisition is required, and this offset acquisition is preferably performed before the first exposure. With reference to FIG. 4, therefore, in the embodiment where system 100 employs manual control, steps 416 and 418 are omitted and a step of obtaining an offset image is performed prior to step 404 (e.g., between steps 402 and 404).

In step 420, the detector is again scrubbed. In step 422, it is determined whether more frames are to be obtained. If no more frames are to be obtained, the method ends. If more frames are to be obtained, the method proceeds to step 424 where the gain of detector 110 is increased. By increasing the gain of detector 110, the pixels generated in response to the second (higher) exposure and the first (lower) exposure are normalized.

Also in step 420, the pixel acquisition resolution is decreased from that used in step 412 for acquiring the second set of image data. As previously discussed, the reducing the pixel acquisition resolution may be accomplished, for example, by pixel binning. That is, by acquiring data from fewer than all of the cells 210 in detector 110. In step 420, the resolution is decreased so that the lower resolution image (e.g., the 1024×1024 cell image) is used in the first (lower) exposure of step 410.

The method of FIG. 4 continues until all frames have been obtained.

Steps 406 and 412 act to reduce the detector read time by reducing the dynamic range for the readout. In step 406, the dose per frame is reduced from that used in step 412. As noted, reducing the dose per frame reduces the photoconductive effects on the FETs, thus allowing the critical time to be reduced. Where fast, multiple frames are to be acquired, as in tomosynthesis, the dynamic range may be reduced for the entire sequence. That is, with fast, multiple frames, x-ray source 120 may be configured such that the dose per frame is reduced as compared to a general-purpose radiographic exposure by a factor in the range of two to ten. That is, the dose per frame may be reduced from a general purpose radio graphic exposure of 1.0 micro Roentgen to a range of between about 0.1 micro Roentgen to 0.5 micro Roentgen. This reduced dynamic range translates into a reduced number of conversion levels. Each conversion level "costs" a fixed amount of time per line. Accordingly, this reduced number of conversion levels can decrease the conversion time a few (2–10) microseconds per line. When used on a detector with 2048 lines, this can amount to 10–20 milliseconds.

Steps 408 and 424 act to reduce the detector read time by decreasing the pixel acquisition resolution. Where fast, multiple frames are to be acquired, as in tomosynthesis, the pixel acquisition resolution may be reduced for the entire sequence. That is, with fast, multiple frames, detector 110 may be configured to provide a low pixel acquisition resolution (e.g., 1024×1024) for the entire sequence. Alternatively, the "low" pixel acquisition resolution (e.g., 1024×1024) can be used in step 412 for obtaining the second image data set, and an even lower pixel acquisition resolution can be used in step 406 for obtaining the first image data set.

A further reduction in the critical time can be obtained by operating with a longer charge integration time (i.e., FET "on" time). This will reduce the amount of first-frame lag as we allow more time constants for more of the charge to be transduced. In general, this will increase the detector read time, as the time needed per scan line read will be increased. The common method to reduce lag is to scrub the detector. A scrub takes an entire detector read interval to complete.

Thus a longer FET on time (several micro seconds per scan line) is much shorter time (several milliseconds) than an additional detector read.

Thus, a method has been described which reduces the time between x-ray acquisitions times to minimize patient motion and minimize potential for detector artifacts. Also, the method minimizes total exam time and allows a fast read of the detector without sacrificing image quality issues. A system incorporating this method has also been described.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another.

What is claimed is:

1. A method for a minimizing artifacts and total exam time between acquisitions in dual or multiple energy imaging, the method comprising:
   (a) exposing a detector to a first exposure from an energy source at a first energy dosage during a first exposure interval;
   (b) after said first exposure interval, obtaining a first image data set during a first read time;
   (c) after said first read time, exposing said detector to a second exposure from said energy source at a second energy dosage during a second exposure interval;
   (d) after said second exposure interval, obtaining a second image data set during a second read time;
   (e) after said second read time, scrubbing said detector;
   (f) after said scrubbing, obtaining a first offset image from said detector;
   (g) after said obtaining said first offset image, obtaining a second offset image from said detector;
   (h) applying said first offset image to compensate for charge retention effects in said first image data set; and
   (i) applying said second offset image to compensate for charge retention effects in the second image data set.

2. The method of claim 1, further comprising:
   after said second read time, exposing said detector to one or more exposures from said energy source; and
   before said scrubbing, obtaining an image data set for each of said one or more exposures from said energy source.

3. The method of claim 1, further comprising:
   repeating (a) through (i) for a plurality of frames.

4. The method of claim 1, wherein said first exposure is a lower dosage than said second exposure.

5. The method of claim 1, wherein said first and second exposures are at a dosage of about 0.1 milli Roentgen to about 0.5 milli Roentgen.

6. The method of claim 1, further comprising:
   after said first read time and before said second exposure interval, changing a gain of said detector.

7. The method of claim 1, further comprising:
   after said first read time and before said second exposure interval, changing a pixel acquisition resolution of said detector.

8. The method of claim 1, wherein said detector comprises a number of cells, and said method further comprises:
   binning pixels corresponding to cells in said detector to decrease a pixel acquisition resolution of said detector.

9. The method of claim 1, wherein said detector is unscrubbed between said first read time and said second read time.

10. A system for dual or multiple energy imaging, the system comprising:
    an energy source configured to emit energy at a first exposure interval at a first energy dosage and at a second exposure interval at a second energy dosage after said first exposure interval;
    a detector comprising a plurality of cells, said detector being configured to:
    receive said energy emitted at said first exposure interval and provide a first image data set indicative of said energy emitted at said first exposure interval,
    receive said energy emitted at said second exposure interval and provide a second image data set indicative of said energy emitted at said second exposure interval,
    provide a first offset image data set, said first offset image data set indicating a retained charge in said plurality of cells at a predetermined amount of time after said second exposure interval, and
    provide a second offset image data set, said second offset image data set indicating a retained charge in said plurality of cells at a predetermined amount of time after said first offset image data set is provided; and
    an image acquisition module configured to apply said first offset image to compensate for said retained charge in said plurality of cells at said predetermined amount of time after said second exposure interval, and apply said second offset image to compensate for said retained charge in said plurality of cells at said predetermined amount of time after said first offset image data set is provided.

11. The system of claim 10, wherein said energy emitted during said first exposure interval is a lower dosage than said energy emitted during said second exposure interval.

12. The system of claim 10, wherein said energy emitted during said first and second exposure intervals are at a dosage of about 0.1 milli Roentgen to about 0.5 milli Roentgen.

13. The system of claim 10, wherein a gain of said detector is changed after receiving said energy emitted during said first exposure interval and before receiving said energy emitted during said second exposure interval.

14. The system of claim 10, wherein a resolution of said first image data set is different than a resolution of said second image data set.

15. The system of claim 10, wherein said first and second image data sets are obtained by binning pixels corresponding to said cells.

16. The system of claim 10, wherein said detector is unscrubbed between said first and second exposure intervals.

17. A method for a minimizing artifacts and total exam time between acquisitions in dual or multiple energy imaging, the method comprising:
    (a) exposing a detector to a first exposure from an energy source at a first energy dosage during a first exposure interval;

(b) after said first exposure interval, obtaining a first image data set during a first read time;

(c) after said first read time, exposing said detector to a second exposure from said energy source at a second energy dosage during a second exposure interval;

(d) after said second exposure interval, obtaining a second image data set during a second read time; and (e) after said first read time and before said second exposure interval, changing a pixel acquisition resolution of said detector.

18. The method of claim 17, further comprising:

after said second read time, exposing said detector to one or more exposures from said energy source; and before said scrubbing, obtaining an image data set for each of said one or more exposures from said energy source.

19. The method of claim 17, further comprising:

repeating (a) through (e) for a plurality of frames.

20. The method of claim 17, wherein said first exposure is a lower dosage than said second exposure.

21. The method of claim 17, wherein said first and second exposures are at a dosage of about 0.1 milli Roentgen to about 0.5 milli Roentgen.

22. The method of claim 17, wherein said detector is unscrubbed between said first read time and said second read time.

23. A method for a minimizing artifacts and total exam time between acquisitions in dual or multiple energy imaging, the method comprising:

(a) exposing a detector to a first exposure from an energy source at a first energy dosage during a first exposure interval;

(b) after said first exposure interval, obtaining a first image data set during a first read time;

(c) after said first read time, exposing said detector to a second exposure from said energy source at a second energy dosage during a second exposure interval;

(d) after said second exposure interval, obtaining a second image data set during a second read time; and (e) after said first read time and before said second exposure interval, changing a gain of said detector.

24. The method of claim 23, further comprising:

after said second read time, exposing said detector to one or more exposures from said energy source; and obtaining an image data set for each of said one or more exposures from said energy source.

25. The method of claim 23, further comprising:

repeating (a) through (e) for a plurality of frames.

26. The method of claim 23, wherein said first exposure is a lower dosage than said second exposure.

27. The method of claim 23, wherein said first and second exposures are at a dosage of about 0.1 milli Roentgen to about 0.5 milli Roentgen.

28. The method of claim 23, further comprising:

after said first read time and before said second exposure interval, changing a pixel acquisition resolution of said detector.

29. The method of claim 23, wherein said detector comprises a number of cells, and said method further comprises:

binning pixels corresponding to cells in said detector to decrease a pixel acquisition resolution of said detector.

30. The method of claim 23, wherein said detector is unscrubbed between said first read time and said second read time.

* * * * *